(12) United States Patent
Kawasaki et al.

(10) Patent No.: US 8,747,486 B2
(45) Date of Patent: Jun. 10, 2014

(54) HUMANOID ELECTRIC HAND

(75) Inventors: Haruhisa Kawasaki, Gifu (JP); Tetuya Mouri, Gifu (JP); Tatuya Hara, Gifu (JP); Hisayuki Shimomura, Kani (JP)

(73) Assignees: Gifu University, Gifu-ken (JP); Dainichi, Co., Ltd., Gifu-ken (JP)

( * ) Notice: Subject to any disclaimer, the term of this patent is extended or adjusted under 35 U.S.C. 154(b) by 0 days.

(21) Appl. No.: 13/824,825

(22) PCT Filed: Sep. 22, 2011

(86) PCT No.: PCT/JP2011/071716
§ 371 (c)(1),
(2), (4) Date: Mar. 18, 2013

(87) PCT Pub. No.: WO2012/039479
PCT Pub. Date: Mar. 29, 2012

(65) Prior Publication Data
US 2013/0175816 A1    Jul. 11, 2013

(30) Foreign Application Priority Data

Sep. 24, 2010  (JP) ................................ 2010-214578

(51) Int. Cl.
*A61F 2/54*  (2006.01)
(52) U.S. Cl.
USPC ............................................. 623/64; 623/24
(58) Field of Classification Search
USPC .................................................. 623/24, 64
See application file for complete search history.

(56) References Cited

U.S. PATENT DOCUMENTS

| 5,888,246 | A | 3/1999 | Gow |
| 6,896,704 | B1 | 5/2005 | Higuchi et al. |
| 2007/0018470 | A1 | 1/2007 | Hayakawa et al. |
| 2010/0010670 | A1 | 1/2010 | Natsukuma et al. |

FOREIGN PATENT DOCUMENTS

| JP | 60090684 A | 5/1985 |
| JP | 60104690 A | 6/1985 |
| JP | 63201086 U | 12/1988 |
| JP | 09510128 A | 10/1997 |
| JP | 2000325375 A | 11/2000 |
| JP | 2001104349 A | 4/2001 |
| JP | 2003165084 A | 10/2003 |
| JP | 2004041279 A | 2/2004 |
| JP | 2004130405 A | 4/2004 |
| JP | 2005088096 A | 4/2005 |
| JP | 2008149444 A | 7/2008 |
| WO | WO 2010/051798 | * 5/2010 |

OTHER PUBLICATIONS

International Search Report issued in PCT/JP2011/071716 mailed Dec. 13, 2011, 2 pages.
English translation of amendments to claims and specification under Article 34, 4 pages.
International Preliminary Report on Patentability, Chapter II, issued in PCT/JP2011/071716, dated May 15, 2012, with English translation, 15 pages.

* cited by examiner

*Primary Examiner* — Bruce E Snow
(74) *Attorney, Agent, or Firm* — Faegre Baker Daniels LLP

(57) ABSTRACT

A humanoid electric hand includes a metacarpophalangeal joint and an interphalangeal joint. The interphalangeal joint bends or extends together with a bending or extending operation of the metacarpophalangeal joint, by linking a finger motor for driving a finger to a worm deceleration mechanism, an output gear of which moves rotationally to bend or extend the metacarpophalangeal joint, and by linking the metacarpophalangeal joint to the interphalangeal joint via a link mechanism.

6 Claims, 8 Drawing Sheets

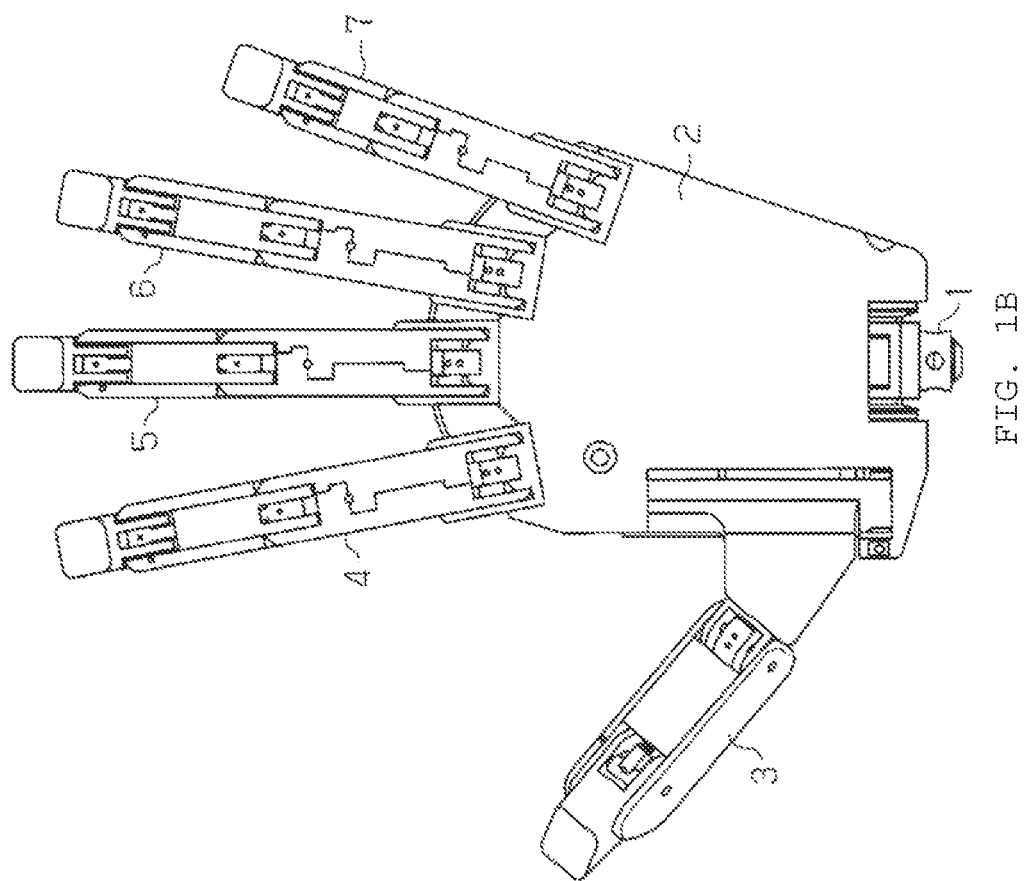
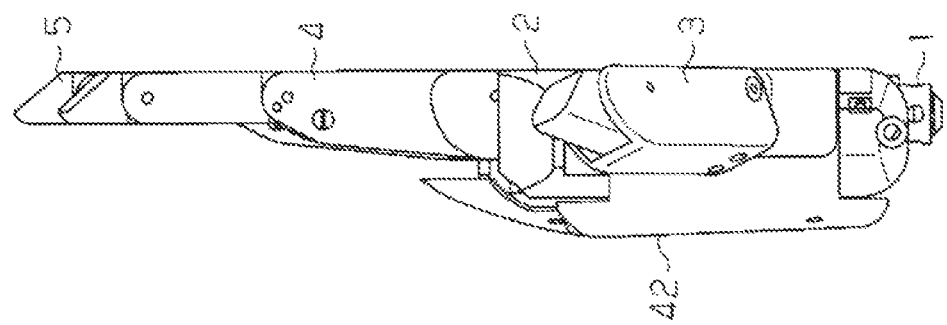
FIG. 1B
FIG. 1A

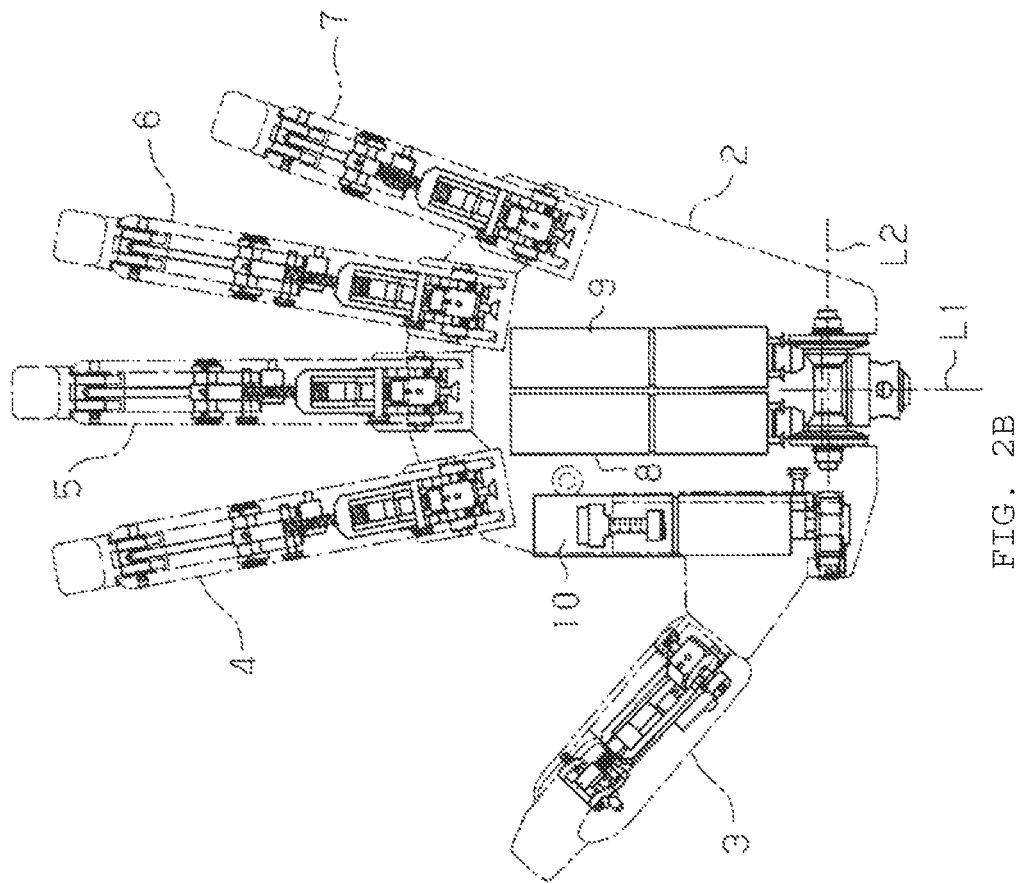
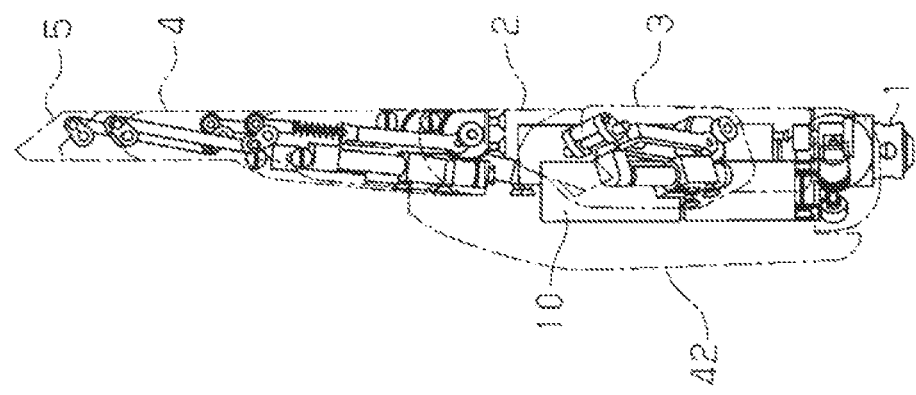

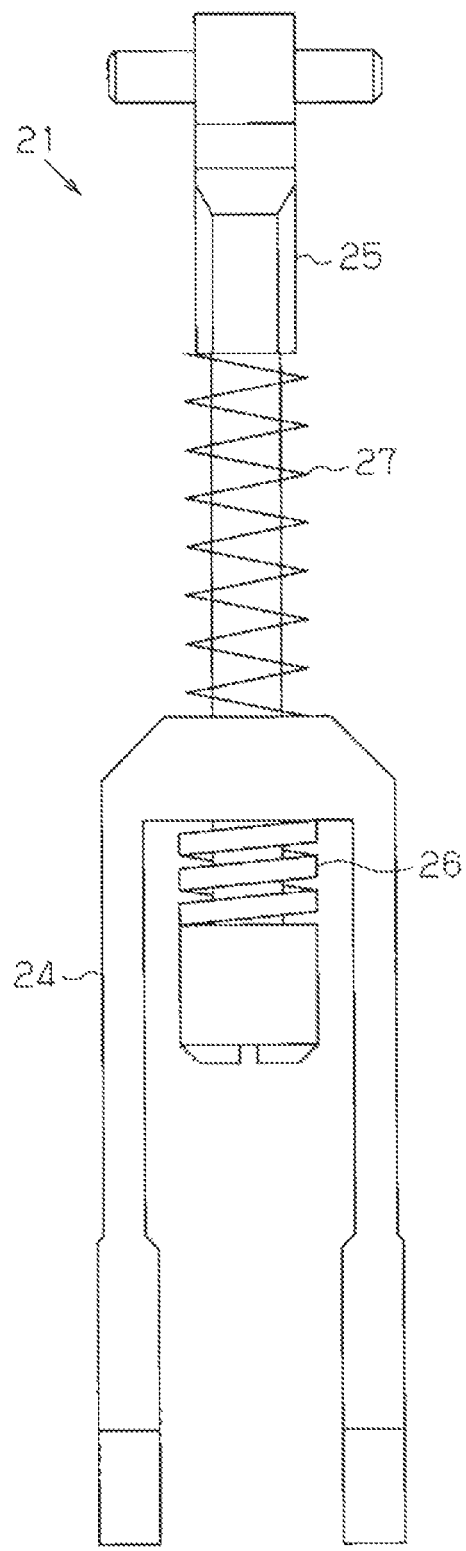
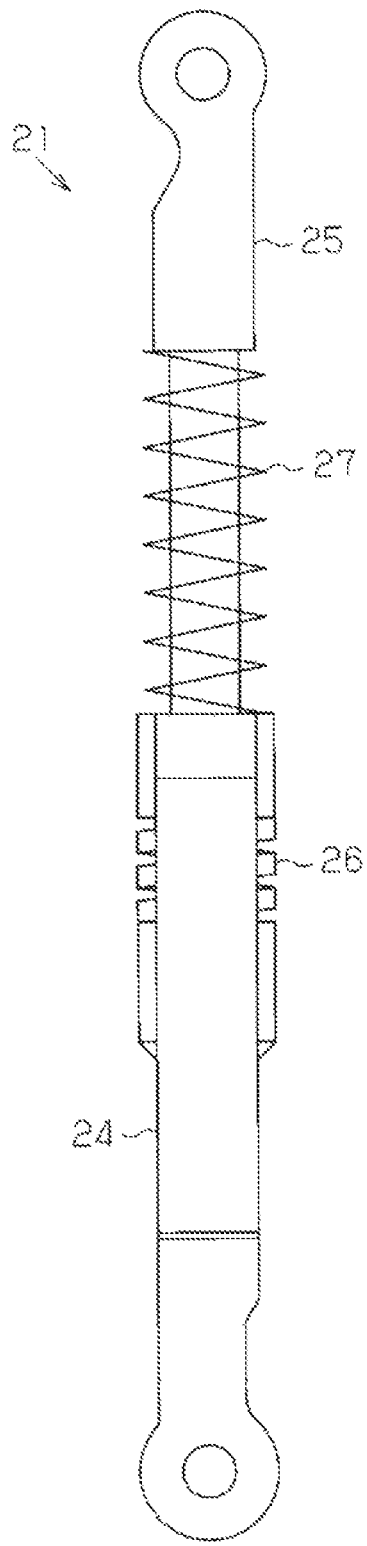
FIG. 5A
FIG. 5B

HUMANOID ELECTRIC HAND

RELATED APPLICATIONS

This application is a national phase application of PCT application PCT/JP2011/071716, internationally filed on Sep. 22, 2011, and is filed pursuant to 35 U.S.C. §371, which claims priority to Japanese Application No. 2010-214578, filed Sep. 24, 2010. Both applications are incorporated by reference in their entirety.

FIELD OF THE INVENTION

The present invention relates to humanoid electric hands used for electric artificial hands, humanoid robots, and the like.

BACKGROUND OF THE INVENTION

Recently, development of humanoid electric hands that are capable of performing holding operations, similarly to human hands, and serve as electric artificial hands or electric hands for humanoid robots has been advanced. According to humanoid electric hands described in Patent Literatures 1 to 3, for example, respective joints of fingers are driven by wires.

As described above, the wires are employed to drive the conventional humanoid electric hands, so that smooth movement of the fingers is realized while avoiding an increase in weight. However, as the wires stretch when used over a long period of time, it is necessary to replace the wires and string the wires again. Accordingly, there are demands for the humanoid electric hands that are light-weighted and easily maintained.

According to the humanoid electric hand described in Patent Literature 3, a motor having a large output is required to drive the fingers other than the thumb, to secure multiple degrees of freedom and a large holding force. This causes an increase in weight of the electric hand. Further, according to the humanoid electric hands described in Patent Literatures 1 to 3, it is inevitable that operations of wrist portions are performed in an unnatural manner because the wrist portions have no degree of freedom. At the time of holding a cup, for example, it is necessary to lean his or her body to adjust the position of the glass, in order to prevent liquid from spilling out of the cup. Further, according to the humanoid electric hands described in Patent Literatures 1 to 3, control sections are provided outside the electric hands. Therefore, it is necessary to route many cables between the electric hands and the control sections. As a result of this, operations of the electric hands may be limited, and operation reliability of the electric hands may be decreased.

RELATED ART DOCUMENTS

Patent Documents

Patent Document 1: Japanese Unexamined Patent Application Publication No. 2000-325375
Patent Document 2: Japanese Unexamined Patent Application Publication No. 2001-104349
Patent Document 3: Japanese Unexamined Patent Application Publication No. 2004-041279

SUMMARY OF INVENTION

It is an object of the present invention to provide a humanoid electric hand that is light-weighted and easily maintained.

In order to solve the above-described problem, a first aspect of the present invention provides a humanoid electric hand in which an interphalangeal joint bends or extends together with a bending or extending operation of a metacarpophalangeal joint, by linking a finger motor for driving a finger to a worm deceleration mechanism, the output gear of which moves rotationally to bend or extend the metacarpophalangeal joint, and by linking the metacarpophalangeal joint to the interphalangeal joint via a link mechanism. The link mechanism includes a driving link formed by two parts linked via elastic members. The elastic members comprise a first elastic member and a second elastic member, the first elastic member compresses when a force in a direction of changing the joint angle of the interphalangeal joint toward joint bending acts on the driving link, the second elastic member has a higher modulus of elasticity than that of the first elastic member and compresses when a force in a direction of changing the joint angle of the interphalangeal joint toward joint extension acts on the driving link.

According to this configuration, when the finger motor rotates, the rotation is decelerated by the worm deceleration mechanism and then allows the output gear to move rotationally. In response to the rotational movement of the output gear, the metacarpophalangeal joint of the finger bends or extends. When the metacarpophalangeal joint bends or extends, the interphalangeal joint that is linked to the metacarpophalangeal joint via the link mechanism bends or extends together with the movement of the metacarpophalangeal joint. Thereby, it is possible to bend or extend the finger by the simple configuration including only the single motor, the worm deceleration mechanism, and the link mechanism. This makes it possible to reduce the weight of the humanoid electric hand. Further, as the finger is bent or extended without using wires, the frequency of replacing parts is reduced and maintenance is facilitated.

A large force may be applied to a fingertip of the humanoid electric hand from an object that is held by the above-described humanoid electric hand. In this case, a self-lock mechanism of the worm deceleration mechanism limits the rotation of the finger motor. Thereby, at the time of holding the object, a joint angle can be maintained to resist the force applied from the object to the fingertip, without depending on power of the finger motor. Therefore, a small-sized motor having a small output can be employed for the finger motor.

Further, according to this configuration, the driving link that is formed by the elastic members and the two parts linked via the elastic members is employed for the link mechanism to link the metacarpophalangeal joint and the interphalangeal joint. Thereby, the driving link expands and contracts in response to an external force applied to the fingertip, causing the joint angle of the interphalangeal joint to change elastically. This makes it possible to allow the joint angle of the interphalangeal joint to correspond to the shape of the holding object. Thus, stable holding operation of the object can be performed.

According to the above-described humanoid electric hand, it is preferable that the second elastic member is arranged so that it does not extend when the first elastic member compresses.

According to this configuration, when the joint angle of the interphalangeal joint is changed elastically toward joint bending, only an elastic force of the first elastic member having the lower modulus of elasticity acts on the driving link, and an elastic force of the second elastic member does not act thereon. Meanwhile, when the joint angle of the interphalangeal joint is changed elastically toward joint extension, the elastic force of the second elastic member, which has the higher modulus of elasticity, acts on the driving link. Therefore, a larger force is necessary when the joint angle of the interphalangeal joint is changed elastically toward joint extension, as compared with the case when the joint angle of the interphalangeal joint is changed elastically toward joint bending.

When holding the object, the force in the direction of changing the joint angle of the interphalangeal joint toward joint extension is applied to the fingertip as a reaction force. According to the above-described configuration, the larger force is required when the joint angle of the interphalangeal joint is changed elastically toward joint extension by the reaction force. This makes it possible to prevent a reduction in the holding force due to extension of the interphalangeal joint while holding the object and to secure the holding force of the object.

According to the above-described humanoid electric hand, it is preferable that a thumb of the electric hand has a mechanism with two degrees of freedom performing a turning operation and a bending or extending operation.

According to this configuration, the holding operation of the object can be performed more easily. Incidentally, the turning operation of the thumb and the bending operations of the rest of the fingers can sandwich and hold the object. At this time, the four fingers, except for the thumb, share and support a pressure of the thumb. This makes it possible to employ the small-sized motor, the maximum output of which is smaller for the finger motor used for the bending or extending operation of each finger. The object can be held appropriately as long as the maximum output of the motor for the turning operation of the thumb can be secured sufficiently.

According to the above-described humanoid electric hand, it is preferable that a motor used for the turning operation of the thumb employs a motor, the maximum output of which is larger than that of the finger motor used for the bending or extending operation of each finger.

According to the above-described humanoid electric hand, it is preferable that a wrist portion of the electric hand has a mechanism with two degrees of freedom performing a pronation or supination operation and a bending or extending operation.

In this case, it is possible to hold the object while keeping the position of an arm in a more natural manner.

According to the above-described humanoid electric hand, it is preferable that the pronation or supination operation and the bending or extending operation of the wrist portion are performed by two motors and a differential deceleration mechanism.

BRIEF DESCRIPTION OF THE DRAWINGS

FIG. 1A is a side view of a humanoid electric hand according to an embodiment of the present invention, and FIG. 1B is a plan view of the humanoid electric hand;

FIG. 2A is a side view showing an internal configuration of the humanoid electric hand, and FIG. 2B is a plan view of the humanoid electric hand;

FIG. 5A is a plan view of a first driving link in the index finger of the humanoid electric hand, and FIG. 5B is a side view of the first driving link;

DETAILED DESCRIPTION OF THE PREFERRED EMBODIMENTS

Figure 3A:
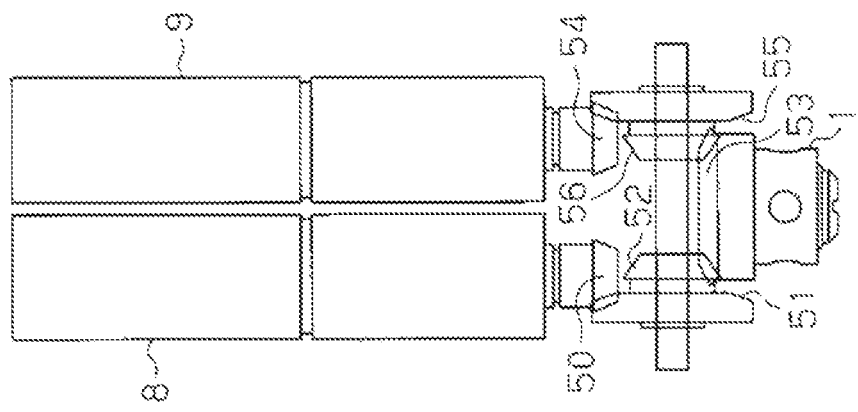
FIG. 3A is a plan view showing a state in which a cover is attached to a wrist driving mechanism in the humanoid electric hand.

Hereinafter, a detailed explanation of an embodiment in which a humanoid electric hand of the present invention is embodied will be given with reference to FIG. 1 to FIG. 10. The humanoid electric hand of this embodiment is used as an electric artificial hand.

As shown in FIG. 1 and FIG. 2, the humanoid electric hand includes a wrist portion 1, a palm portion 2, and five fingers of a thumb 3, an index finger 4, a middle finger 5, a ring finger 6 and a little finger 7. The wrist portion 1 corresponds to a human wrist. The palm portion 2 corresponds to a human palm.

An artificial skin is attached on the surface of the electric hand. Further, a pressure sensor is arranged between the artificial skin and a frame of each of the fingers. A gel-like high functional material, having a durometer hardness of 12, tensile strength of 9.6 MPa and weight of 64 g, is used as the artificial skin.

(Configuration of Wrist Portion)

Next, a configuration of the wrist portion 1 will be explained with reference to FIG. 3.

Figure 3B:
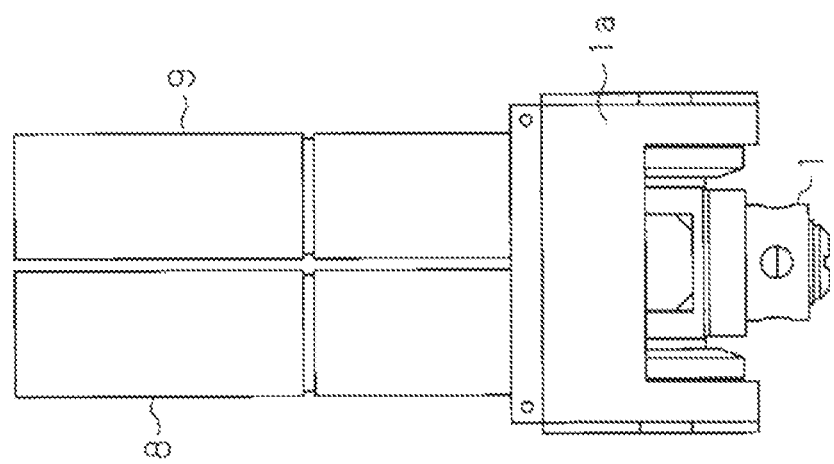
FIG. 3B is a plan view showing a state in which the cover is removed from the wrist driving mechanism.

The wrist portion 1 is driven by a wrist driving mechanism shown in FIG. 3. The wrist driving mechanism includes two wrist motors 8 and 9. As shown in FIG. 2, the wrist motors 8 and 9 are provided inside the palm portion 2 of the humanoid electric hand.

A first bevel gear 50 is fixed to an output shaft of the wrist motor 8 that is provided on the left side in FIG. 3. The first bevel gear 50 engages with a second bevel gear 51. The first and second bevel gears 50 and 51 are respectively arranged with their axes being orthogonal to each other. A third bevel gear 52 is linked to the second bevel gear 51 to be able to rotate with the second bevel gear 51. The third bevel gear 52 engages with a fourth bevel gear 53. The third and fourth bevel gears 52 and 53 are respectively arranged with these axes being orthogonal to each other.

A first bevel gear 54 is fixed to an output shaft of the wrist motor 9 that is provided on the right side in FIG. 3. The first bevel gear 54 engages with a second bevel gear 55. The first and second bevel gears 54 and 55 are respectively arranged with these axes being orthogonal to each other. A third bevel gear 56 is linked to the second bevel gear 55 to be able to rotate with the second bevel gear 55. The third bevel gear 56 engages with the fourth bevel gear 53. The third and fourth bevel gears 56 and 53 are respectively arranged with these axes being orthogonal to each other. The second bevel gear 55 and the third bevel gear 56 are arranged coaxially with the second bevel gear 51 and the third bevel gear 52. The above-described bevel gears 50 to 56 form a differential deceleration mechanism.

(Operation of Wrist Portion)

Next, an operation of the wrist portion 1 will be explained. When the wrist motors 8 and 9 are rotated in directions opposite to each other, according to the above-described wrist driving mechanism, the fourth bevel gear 53 does not rotate, and the second bevel gears 51 and 55 and the third bevel gears 52 and 56 respectively rotate in the same direction. Thereby, the wrist portion 1 moves rotationally around an axis L2, as shown in FIG. 2B, with respect to the palm portion 2. This causes the wrist portion 1 to move to bend or extend.

Meanwhile, when the wrist motors 8 and 9 are rotated in the same direction, the second bevel gear 51 and the third bevel gear 52 on the left side in FIG. 3 and the second bevel gear 55 and the third bevel gear 56 on the right side in FIG. 3 respectively rotate in the directions opposite to each other. Thus, the fourth bevel gear 53 rotates, causing the wrist portion 1 to move rotationally around an axis L1, as shown in FIG. 2B, with respect to the palm portion 2. Thereby, the wrist portion 1 moves to pronate or supinate. Thus, the wrist portion 1 performs pronation or supination operation and bending or extending operation by driving the gears. In other words, the wrist portion 1 is configured as a mechanism with two degrees of freedom.

(Configuration of Index Finger and the Like)

Next, a configuration of the index finger 4 will be explained with reference to FIG. 4 and FIG. 5. According to the humanoid electric hand, configurations of the middle finger 5, the ring finger 6 and the little finger 7 are almost common to the configuration of the index finger 4, except for the lengths of respective sections.

Figure 4:
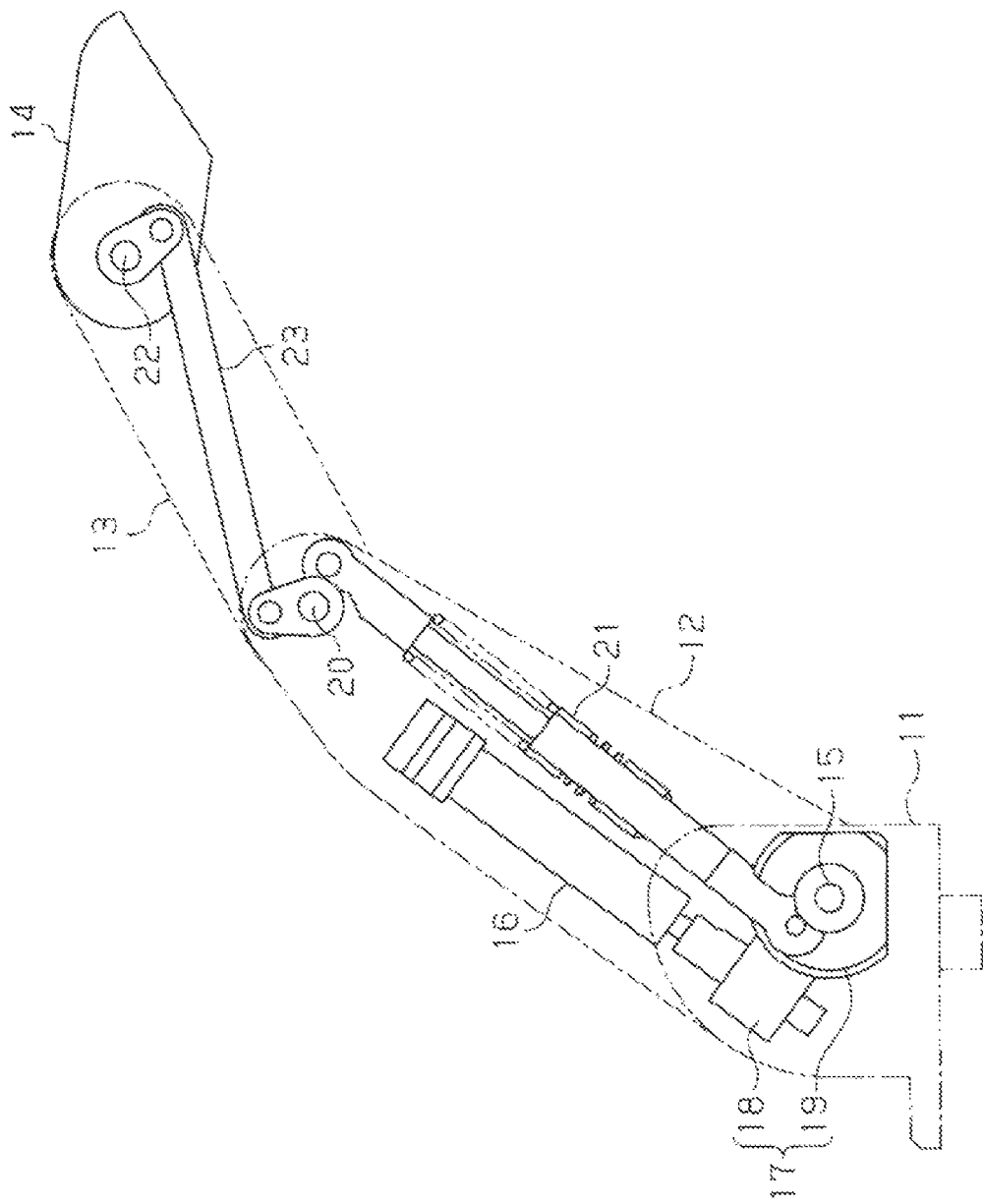
FIG. 4 is a side view showing an internal configuration of an index finger of the humanoid electric hand.

As shown in FIG. 4 and FIG. 5, the index finger 4 is formed by a base portion 11 that is fixed to the palm portion 2, and three sections of a base section 12, a middle section 13, and a distal section 14. A finger motor 16 is provided inside the base section 12. The finger motor 16 allows a metacarpophalangeal joint 15, as a joint between the base portion 11 and the base section 12, to perform a bending or extending operation. To an output shaft of the finger motor 16, a worm (screw gear) 18, as an input gear of a worm deceleration mechanism 17, is fixed. The worm 18 engages with a worm wheel (helical gear) 19 that is fixed to the base portion 11. The worm wheel 19 corresponds to an output gear of the worm deceleration mechanism 17. The base section 12 of the index finger 4 is supported to be able to move rotationally with respect to a shaft of the worm wheel 19. The shaft of the worm wheel 19 is the metacarpophalangeal joint 15.

A proximal interphalangeal joint 20, as a joint between the base section 12 and the middle section 13, is provided at the tip end of the base section 12. The middle section 13 is supported by the proximal interphalangeal joint 20 to be able to move rotationally. A first driving link 21 is disposed between the proximal interphalangeal joint 20 and the metacarpophalangeal joint 15. The base end of the first driving link 21 is arranged at a position eccentric from the metacarpophalangeal joint 15 and is supported to be able to move rotationally with respect to the base portion 11. The tip end of the first driving link 21 is arranged at a position eccentric from the proximal interphalangeal joint 20 and is supported to be able to move rotationally with respect to the middle section 13.

A distal interphalangeal joint 22, as a joint between the middle section 13 and the distal section 14, is provided at the tip end of the middle section 13. The distal section 14 is supported by the distal interphalangeal joint 22 to be able to move rotationally. A second driving link 23 is disposed between the distal interphalangeal joint 22 and the proximal interphalangeal joint 20. The base end of the second driving link 23 is arranged at a position eccentric from the proximal interphalangeal joint 20 and is supported to be able to move rotationally with respect to the base section 12. The tip end of the second driving link 23 is arranged at a position eccentric from the distal interphalangeal joint 22 and is supported to be able to move rotationally with respect to the distal section 14.

Next, a configuration of the first driving link 21 will be explained with reference to FIG. 5.

As shown in FIG. 5, the first driving link 21 is formed by two parts of a first rod 24 and a second rod 25. The first driving link 21 expands and contracts by translational motion of the first rod 24 and the second rod 25.

The first rod 24 and the second rod 25 are linked via two coil springs 26 and 27 as elastic members. Springs with different moduli of elasticity are employed for the two coil springs 26 and 27. The coil spring 26, corresponding to a second elastic member, has the modulus of elasticity higher than that of the coil spring 27, corresponding to a first elastic member. When the first driving link 21 contracts, the coil spring 27 is compressed. When the first driving link 21 expands, the coil spring 26 is compressed. Thus, the length of the first driving link 21 changes elastically by a function of a tensile or compressive load.

Incidentally, the coil spring 26 is disposed not to be subjected to compression or tension when an external force does not act on the first driving link 21. Moreover, both ends of the coil spring 26 are not fixed to the first rod 24 and the second rod 25 and are separated from the first rod 24 and the second rod 25 when the coil spring 26 expands to its natural length. Therefore, the coil spring 26 is arranged so that it does not extend when the first driving link 21 contracts together with the compression of the coil spring 27.

(Operation of Index Finger and the Like)

Next, an operation of the index finger 4 will be explained. As described above, the configurations of the middle finger 5, the ring finger 6 and the little finger 7 are almost common to that of the index finger 4, and operations thereof are similar to that of the index finger 4.

When the finger motor 16 rotates, the worm 18 rotates and then the worm wheel 19 rotates. With the humanoid electric hand, the worm wheel 19 is fixed to the palm portion 2. Accordingly, when the finger motor 16 rotates, the base section 12, in which the finger motor 16 is provided, moves rotationally around the metacarpophalangeal joint 15 as the shaft of the worm wheel 19. This causes the base section 12 to bend or extend around the metacarpophalangeal joint 15 with respect to the base portion 11.

When the bending operation around the metacarpophalangeal joint 15 is performed, the movement is transferred via the first driving link 21 to the proximal interphalangeal joint 20, and a bending operation of the proximal interphalangeal joint 20 is performed. When the bending operation of the proximal interphalangeal joint 20 is performed, the movement is further transferred via the second driving link 23 to the distal interphalangeal joint 22, and a bending operation of the distal interphalangeal joint 22 is performed.

Meanwhile, when the extending operation around the metacarpophalangeal joint 15 is performed, the movement is transferred via the first driving link 21 and the second driving link 23 to the proximal interphalangeal joint 20 and the distal interphalangeal joint 22, respectively, and extending operations of the proximal interphalangeal joint 20 and the distal interphalangeal joint 22 are performed, respectively. Thus, the index finger 4 is configured to perform the bending or extending operations of the proximal interphalangeal joint 20 and the distal interphalangeal joint 22, together with the bending or extending operation of the metacarpophalangeal joint 15.

When a large external force acts on a fingertip, a self-lock function of the worm deceleration mechanism limits the rotation of the finger motor 16. In other words, the index finger 4 does not have back-drivability. Accordingly, even when the external force is applied to the fingertip while the finger motor 16 is in a stopped state, the metacarpophalangeal joint 15 is maintained to have a constant joint angle.

Meanwhile, the first driving link 21 can expand and contract elastically. Therefore, when a force in the direction of extending the index finger 4 is applied to the fingertip of the index finger 4, the first driving link 21 expands and the proximal interphalangeal joint 20 and the distal interphalangeal joint 22 respectively extend. Hence, when the fingertip of the index finger 4 is brought into contact with an object while the finger motor 16 performs the bending operation, and when its reaction force is applied to the fingertip, the proximal interphalangeal joint 20 and the distal interphalangeal joint 22 respectively extend, and the index finger 4 does not bend further. As a result of this, the joint angles of the proximal interphalangeal joint 20 and the distal interphalangeal joint 22 automatically correspond to the shape of the holding object.

At this time, the coil spring 26 is compressed as the first driving link 21 extends. Thus, an elastic force is generated by the compression of the coil spring 26, which can resist the reaction force that is applied to the fingertip when holding the object. This makes it possible to prevent a reduction in a holding force of the humanoid electric hand while holding the object due to the expansion of the interphalangeal joints 20 and 22. Meanwhile, when the fingertip is brought into contact with an obstacle from a nail side, the first driving link 21 contracts and the proximal interphalangeal joint 20 and the distal interphalangeal joint 22 bend. Such elastic deformation of the first driving link 21 reduces a force acting on the respective parts of the fingers due to contact with the obstacle.

It should be noted that, as described above, the coil spring 26 is arranged so that it does not extend when the first driving link 21 reduces its length, together with the compression of the coil spring 27. Therefore, only an elastic force of the coil spring 27, which has the relatively lower modulus of elasticity, acts on the first driving link 21 at this time. Thus, even when the force applied to the fingertip is not very large, the proximal interphalangeal joint 20 and the distal interphalangeal joint 22 elastically bend in response to the contact with the obstacle.

(Configuration of Thumb)

Next, a configuration of the thumb 3 will be explained with reference to FIG. 6 to FIG. 9.

Figure 6:
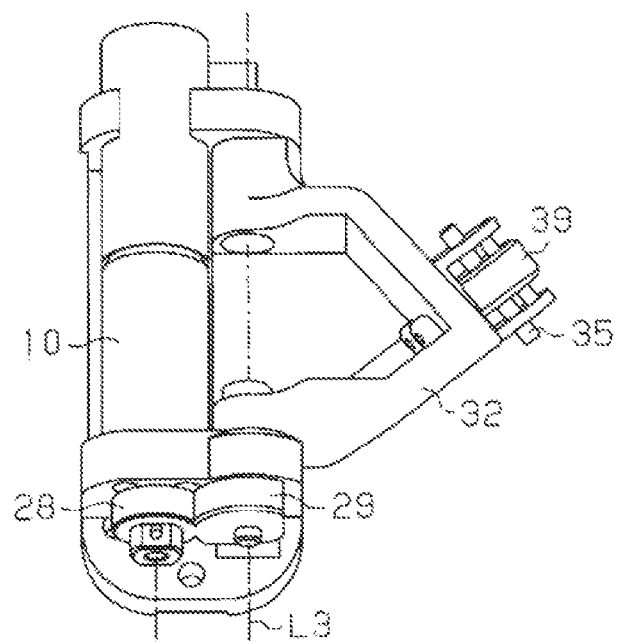
FIG. 6 is a perspective view showing the base of a thumb of the humanoid electric hand.

A thumb turning mechanism is provided in the thumb 3. The thumb turning mechanism allows the thumb 3 to turn at its base portion. As shown in FIG. 6, the thumb turning mechanism includes a thumb turning motor 10 fixed to the palm portion 2. The thumb turning motor 10 is provided inside the palm portion 2 of the humanoid electric hand (refer to FIG. 2). A first spur gear 28 is fixed to an output shaft of the thumb turning motor 10. The first spur gear 28 engages with a second spur gear 29. The second spur gear 29 is fixed to a base portion 32 of the thumb 3. The thumb turning motor 10 employs a motor, the maximum output of which is larger than those of the finger motor 16 and a thumb motor 36.

Figure 7:
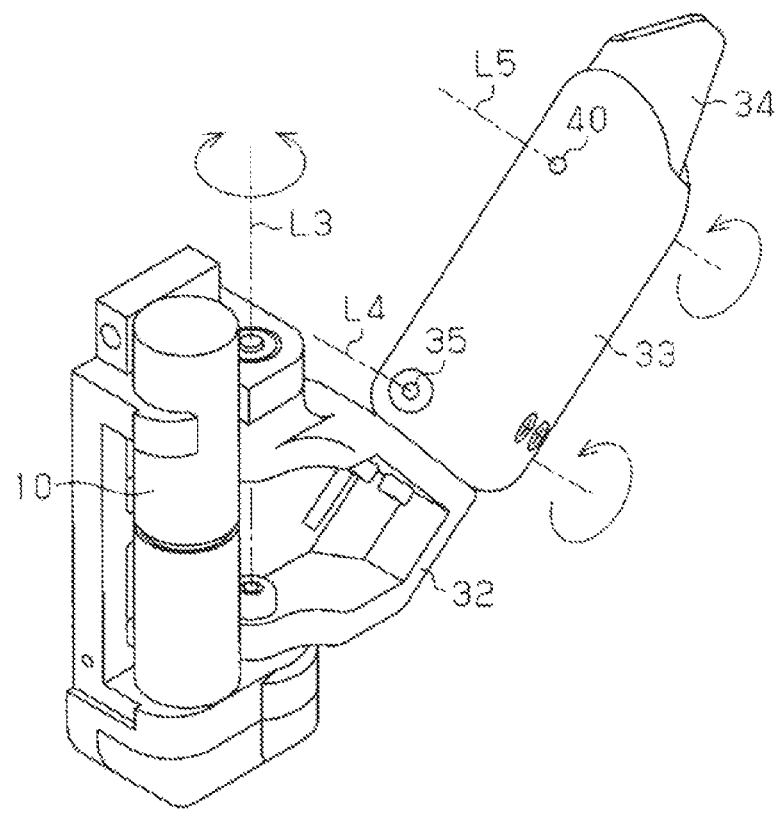
FIG. 7 is a perspective view of the thumb of the humanoid electric hand.

Meanwhile, the thumb 3 has two sections of a base section 33 and a distal section 34, as shown in FIG. 7. The thumb 3 has a metacarpophalangeal joint 35 as a joint between the base portion 32 and the base section 33, and an interphalangeal joint 40 as a joint between the base section 33 and the distal section 34.

Figure 8:
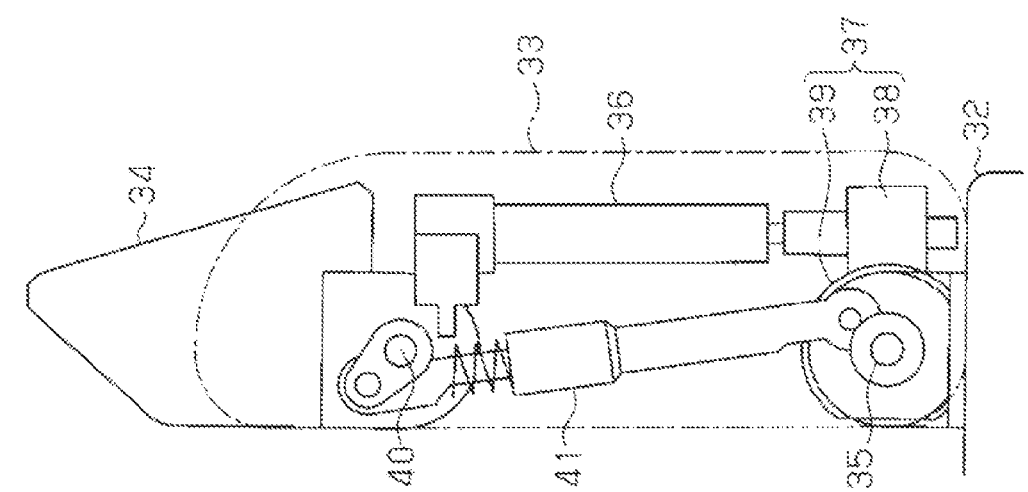
FIG. 8 is a side view showing an internal configuration of the thumb of the humanoid electric hand.

As shown in FIG. 8, the thumb motor 36 for bending or extending the metacarpophalangeal joint 35 is provided inside the base section 33. To an output shaft of the thumb motor 36, a worm 38, as an input gear of a worm deceleration mechanism 37, is fixed. The worm 38 engages with a worm wheel 39 that is fixed to the base portion 32 of the thumb 3. The worm wheel 39 corresponds to an output gear of the worm deceleration mechanism 37. The base section 33 is supported to be able to move rotationally with respect to a shaft of the worm wheel 39. The shaft of the worm wheel 39 is the metacarpophalangeal joint 35 of the thumb 3.

The interphalangeal joint 40 is provided at the tip end of the base section 33. The distal section 34 is supported by the interphalangeal joint 40 to be able to move rotationally. A thumb driving link 41 is disposed between the interphalangeal joint 40 and the metacarpophalangeal joint 35. The base end of the thumb driving link 41 is arranged at a position eccentric from the metacarpophalangeal joint 35 of the thumb 3 and is supported to be able to move rotationally with respect to the base portion 32 (worm wheel 39). The tip end of the thumb driving link 41 is arranged at a position eccentric from the interphalangeal joint 40 of the thumb 3 and is supported to be able to move rotationally with respect to the distal section 34.

Figure 9:
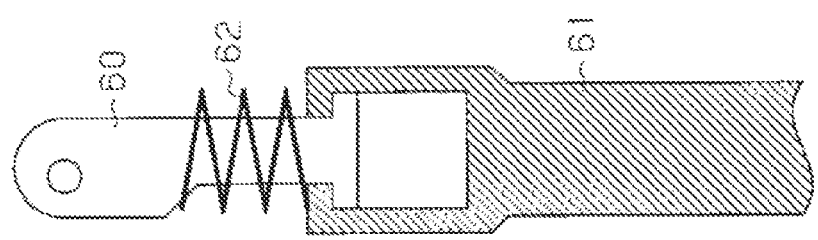
FIG. 9 is a plan view showing a plan configuration of a thumb driving link in the thumb.

As shown in FIG. 9, the thumb driving link 41 is formed by two parts of a first rod 60 and a second rod 61. The thumb driving link 41 expands and contracts by translational motion of the first rod 60 and the second rod 61.

The first rod 60 and the second rod 61 are linked via a coil spring 62 as an elastic member. The coil spring 62 is compressed by the first rod 60 and the second rod 61 as the length of the thumb driving link 41 decreases.

Thus, the thumb driving link 41 is formed by the two parts that are linked via the elastic member and is configured to be able to expand and contract elastically. It should be noted that the elastic expansion and contraction of the thumb driving link 41 are allowed only within a range of a natural length of the thumb driving link 41, that is, within the range equal to or smaller than the length at the time when the external force is not applied thereto.

(Operation of Thumb)

Next, an operation of the above-described thumb 3 will be explained.

When the thumb turning motor 10 rotates, the rotation is transferred via the first spur gear 28 and the second spur gear 29 to the base portion 32. This allows the thumb 3 to turn.

Meanwhile, when the thumb motor 36 rotates, the rotation is decelerated via the worm deceleration mechanism 37 and then transferred to the metacarpophalangeal joint 35. This causes the metacarpophalangeal joint 35 to bend or extend. When the metacarpophalangeal joint 35 bends or extends like this, the movement is transferred via the thumb driving link 41 to the interphalangeal joint 40. As a result of this, the interphalangeal joint 40 also bends or extends together with the metacarpophalangeal joint 35.

It should be noted that, in the thumb 3, the thumb driving link 41 can reduce its length elastically. Therefore, when the fingertip is brought into contact with the obstacle from the nail side, a compressive load acts on the thumb driving link 41, resulting in a reduction in the length of the thumb driving link 41 elastically. Thus, the force acting on the respective parts of the finger, due to hitting on the obstacle, is also reduced in the thumb 3.

Meanwhile, the elastic deformation of the thumb driving link 41 is allowed only in a direction of reducing its length and is not allowed in a direction of increasing its length. Therefore, the pressure of the thumb 3 applied to the object is not reduced while holding the object, due to the reaction force applied from the object to the fingertip to expand the interphalangeal joint 40 of the thumb 3.

(Configuration of Control Section)

Next, a configuration of a control section of the humanoid electric hand will be explained.

Figure 10:
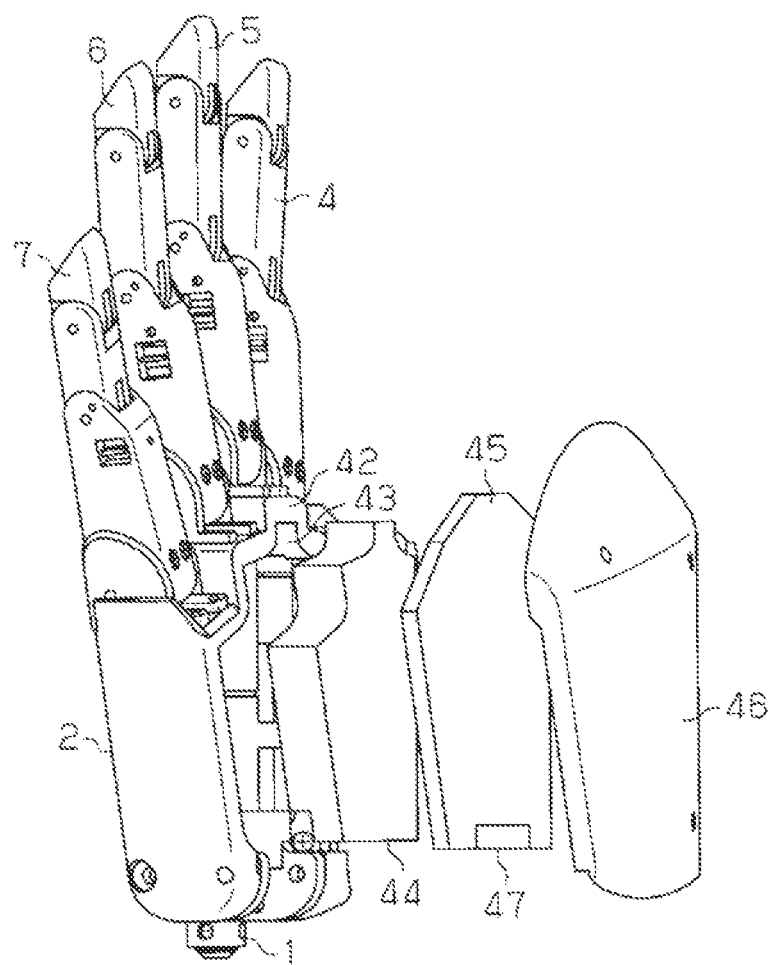
FIG. 10 is an exploded perspective view of the humanoid electric hand.

Boards for controlling, including driving circuits of the motors, are provided inside a back portion 42 of the humanoid electric hand. Namely, as shown in FIG. 10, a recessed portion 43 is formed in the back portion 42. The recessed portion 43 accommodates a driver board 44 on which the driving circuits of the motors are provided, and a control board 45 on which a control circuit is provided. A hand cover 46 is attached to the back portion 42 to cover the recessed portion 43. The control circuit of the control board 45 has an input/output interface that functions to receive as inputs encoder signals of the respective motors and signals of the pressure sensors attached to the electric hand and the like and to output PWM signals to the respective motors.

A LAN terminal 47 is provided to the control board 45. The control circuit of the control board 45 has a LAN function to communicate with external devices. The control circuit also has a computation function to perform a computation of the outputs based on the inputs. With the LAN function, communication with an electromyography measurement system is also possible. The control circuit performs the computation of the holding force and the angle of the interphalangeal joint based on input signals from the electromyography measurement system and outputs the PWM signals to the respective motors.

The PWM signals outputted from the control circuit are inputted to the driving circuit of the driver board 44. The driving circuit amplifies power of the inputted PWM signals and outputs these to the respective motors.

An FPGA is employed for an integrated circuit provided on the control circuit. The FPGA is reprogrammable in the field.

The following effects can be obtained according to the humanoid electric hand described thus far.

(1) The finger motor 16 is linked to the worm deceleration mechanism 17. The worm wheel 19, which serves as the output gear of the worm deceleration mechanism 17, moves rotationally to bend or extend the metacarpophalangeal joint 15. Further, as the metacarpophalangeal joint 15 and the interphalangeal joints 20 and 22 are linked via the link mechanisms, the interphalangeal joints 20 and 22 bend or extend together with the bending or extending operation of the metacarpophalangeal joint 15. Meanwhile, the thumb motor 36 is linked to the worm deceleration mechanism 37. The worm wheel 39, which serves as the output gear of the worm deceleration mechanism 37, moves rotationally to bend or extend the metacarpophalangeal joint 35. Further, as the metacarpophalangeal joint 35 and the interphalangeal joint 40 are linked by the link mechanism, the interphalangeal joint 40 bends or extends together with the bending or extending operation of the metacarpophalangeal joint 35.

Namely, when the finger motor 16 rotates, the rotation is decelerated by the worm deceleration mechanism 17 and then allows the worm wheel 19 to move rotationally. In response to the rotational movement of the worm wheel 19, the metacarpophalangeal joint 15 of the finger bends or extends. When the metacarpophalangeal joint 15 bends or extends, the interphalangeal joints 20 and 22 bend or extend together with the movement of the metacarpophalangeal joint 15. Meanwhile, when the thumb motor 36 rotates, the rotation is decelerated by the worm deceleration mechanism 37 and then allows the worm wheel 39 to move rotationally. In response to the rotational movement of the worm wheel 39, the metacarpophalangeal joint 35 of the finger bends or extends. When the metacarpophalangeal joint 35 bends or extends, the interphalangeal joint 40 bends or extends together with the movement of the metacarpophalangeal joint 35.

According to this configuration, it is possible to bend or extend the fingers by the simple configuration including only the single motors 16 and 36, the worm deceleration mechanisms 17 and 37, and the link mechanisms. This makes it possible to reduce the weight of the humanoid electric hand. Further, as the fingers are bent or extended without using wires, the frequency of replacing parts is reduced, and maintenance is facilitated. Thus, according to the above-described humanoid electric hand, it is possible to realize the weight reduction and to facilitate the maintenance.

(2) A large force may be applied to the fingertip of the humanoid electric hand from the object that is held by the humanoid electric hand. In this case, a self-lock mechanism of the worm deceleration mechanism 17 can maintain the constant joint angle of the metacarpophalangeal joint 15. Thereby, at the time of holding the object, the joint angle of the metacarpophalangeal joint 15 can be maintained to resist the force applied from the object to the fingertip, without depending on power of the finger motor 16. Therefore, a small-sized motor having a small output can be employed for the finger motor 16.

(3) The driving link 21 formed by the coil spring 26, the coil spring 27, the first rod 24 and the second rod 25 that are linked via the coil spring 26 and the coil spring 27 is employed for the link mechanism to link the metacarpophalangeal joint 15 to the interphalangeal joints 20 and 22 of each of the index finger 4, the middle finger 5, the ring finger 6 and the little finger 7. Further, the thumb driving link 41 formed by the coil spring 62, the first rod 60 and the second rod 61 that are linked via the coil spring 62 is employed for the link mechanism to link the metacarpophalangeal joint 35 and the interphalangeal joint 40 of the thumb 3. According to this configuration, the joint angles of the interphalangeal joints 20, 22 and 40 correspond to the shape of the holding object. Thus, stable holding operation of the object can be performed.

(4) The coil spring 27 and the coil spring 26 are provided as the elastic members to link the first rod 24 and the second rod 25 of the first driving link 21. When the force in the direction of elastically changing the joint angles of the proximal interphalangeal joint 20 and the distal interphalangeal joint 22 toward joint bending acts on the first driving link 21, the coil spring 27 is compressed to generate the elastic force resisting the force. When the force in the direction of elastically changing the joint angles of the proximal interphalangeal joint 20 and the distal interphalangeal joint 22 toward joint extension acts on the first driving link 21, the coil spring 26 is compressed to generate the elastic force resisting the force. Further, the coil spring 26 has the higher modulus of elasticity than that of the coil spring 27. Furthermore, the coil spring 26 is arranged so that it does not extend when the coil spring 27 is compressed. Therefore, when the joint angles of the interphalangeal joints 20 and 22 change elastically in response to the expansion and contraction of the first driving link 21, a larger force is necessary in the direction of extending the finger. Thus, it is possible to automatically adjust the joint angles of the interphalangeal joints and, at the same time, to resist the reaction force applied to the fingertips at the time of holding the object. This makes it possible to prevent a reduction in the holding force due to the extension of the fingers and to secure the holding force of the object.

(5) The finger motors 16 and the thumb motor 36 are provided inside the respective fingers. Therefore, all the necessary configurations to bend or extend the respective fingers can be provided inside the respective fingers.

(6) The thumb 3 performs the turning operation and the bending or extending operation. In other words, the thumb 3 is configured as the mechanism with two degrees of freedom. This makes it possible to perform the holding operation of the object more easily.

(7) The thumb turning motor 10 performs the turning operation of the thumb 3 and is provided inside the palm portion 2 of the electric hand. This makes it possible to make the thumb 3 of the electric hand more compact.

(8) The thumb motor 36 performs the bending or extending operation of the thumb 3 and is provided inside the base section 33 of the thumb 3 that has limited installation space. As a result of this, it is difficult to employ a large-sized motor for the thumb motor 36. Meanwhile, the thumb turning motor 10 is provided inside the palm portion 2 that has sufficient installation space. Consequently, it is possible to employ the large-sized motor for the thumb turning motor 10. Therefore, the power of the thumb turning motor 10 can compensate for a power shortage of the thumb motor 36. As a result of this, the humanoid electric hand can generate a large holding force.

(9) The wrist portion 1 performs the pronation or supination operation and the bending or extending operation. In other words, the wrist portion 1 is configured as the mechanism with two degrees of freedom. This makes it possible to hold the object while keeping the position of the arm in a more natural manner.

(10) The motor, the maximum output of which is larger than that of the finger motor 16, is employed for the thumb turning motor 10. The pressure by the turning operation of the thumb 3 toward the palm side and the pressures by the bending operations of the remaining four fingers allow the above-described humanoid electric hand to sandwich and hold the object. At this time, the respective fingers except for the thumb 3 share and receive the pressure of the thumb 3. Therefore, it is not necessary to increase the pressures by the bending of the respective fingers, except for the thumb 3, more than necessary, in order to secure the holding force. This makes it possible to employ the motor having the larger maximum output for the thumb turning motor 10 only and to employ small-sized motors having the smaller maximum outputs for the finger motors 16. As a result of this, downsizing and the weight reduction of the humanoid electric hand can be made possible.

(11) The pronation or supination operation and the bending or extending operation of the wrist portion 1 are performed by the two wrist motors 8 and 9 and the differential deceleration mechanism 50 to 56. Thus, the above-described two operations can be performed by the relatively simple configuration.

(12) The wrist motors 8 and 9 are provided inside the palm portion 2 of the electric hand. Thus, all the driving mechanisms of the electric hand can be provided inside the electric hand. When it is used as the electric artificial hand, it may be necessary to set the wrist motors 8 and 9 on the side of a forearm from the wrist portion 1. In this case, the length of one arm to which the electric hand is attached becomes too long, if the length from an amputated position of the forearm to the lost wrist is not long enough, causing an imbalance between the arm and the other arm. According to the present invention, however, the wrist motors 8 and 9 are provided inside the palm portion 2 and therefore, the electric hand can be attached to the amputated position of the forearm, irrespective of the position of the amputation of the forearm. In other words, the electric hand can be attached properly only by adjusting the length of a socket interposed between the amputated position and the electric hand.

(13) The driver board 44 and the control board 45 include the boards for controlling having the driving circuits of the motors and are provided inside the back portion 42 of the electric hand. Therefore, only a signal cable for transmitting command signals and a power cable have to be wired between the electric hand and the outside. Thus, the movement of the electric hand is not limited by the cables. Further, it is less likely that operation reliability of the electric hand decreases due to a break in the cables.

(14) The elastic change of the joint angle of the interphalangeal joint 40 of the thumb 3 is limited to the change toward joint bending. Therefore, the pressure of the thumb 3 to the object is not reduced due to the extension of the interphalangeal joint 40 of the thumb 3 by the reaction force applied from the object to the fingertip, while holding the object. Consequently, the holding force can be secured with more reliability.

The above-described embodiment may be modified as follows:

According to the above-described embodiment, the coil spring 26 is set without fixing both ends, so that the coil spring 26 does not extend when the first driving link 21 contracts together with the compression of the coil spring 27. Even if one of the ends of the coil spring 26 is fixed, the coil spring 26 does not extend when the first driving link 21 is contracted, as long as the other end is not fixed. Accordingly, when the coil spring 26 is set without fixing at least one end, the force required to elastically change the joint angles of the interphalangeal joints 20 and 22 toward joint extension can be made larger than the force required to elastically change the joint angles toward bending.

According to the above-described embodiment, it is possible to change the configurations of the wrist driving mechanism, the link mechanisms of the respective fingers, and the worm deceleration mechanisms 17 and 37 at will, as long as these functions can be realized.

According to the above-described embodiment, the driver board 44 and the control board 45 may be provided outside the electric hand, when the routing of the cables presents no problem.

According to the above-described embodiment, the wrist motors 8 and 9 may be set on the side of the forearm from the wrist portion 1, when sufficient installation space can be secured on the side of the forearm from the wrist portion 1.

According to the above-described embodiment, the wrist portion 1 may be configured as the mechanism with one degree of freedom that performs either one of the pronation or supination operation and the bending or extending operation. Moreover, the degree of freedom of the wrist portion 1 may be "0".

According to the above-described embodiment, the thumb turning motor 10 may be provided inside the thumb 3 when sufficient installation space can be secured in the thumb 3.

According to the above-described embodiment, the thumb 3 may be configured as the mechanism with one degree of freedom that performs the bending or extending operation only.

According to the above-described embodiment, the finger motors 16 and the thumb motor 36 may be set in the palm portion 2 of the electric hand, when sufficient installation space cannot be secured in the fingers.

According to the above-described embodiment, elastic members such as flat springs and rubber may be used, instead of the coil springs, as the elastic members to be disposed between the first rod 24 and the second rod 25 that form the driving links 21 and 41. As long as the elastic members can expand and contract along the axes in response to the tensile or compressive load acting on the driving links 21 and 41, it is also possible to automatically adjust the joint angles to correspond to the shape of the holding object and to hold the object stably.

According to the above-described embodiment, the first driving link 21, formed by the coil springs 26 and 27 as the elastic members and the first rod 24 and the second rod 25 linked via the coil springs 26 and 27, and the thumb driving link 41 are employed for the link mechanisms to link the metacarpophalangeal joints 15 and 35 to the interphalangeal joints 20, 22 and 40, respectively. However, the lengths of the driving links 21 and 41 may be fixed when it is not necessary to adjust the joint angles to correspond to the shape of the holding object.

According to the above-described embodiment, the humanoid electric hand of the present invention is applied to the electric artificial hand, but it may be applied to an electric hand for a humanoid robot.

REFERENCE SIGNS LIST

1 . . . wrist portion, 1a . . . cover, 2 . . . palm portion, 3 . . . thumb (32 . . . base portion, 33 . . . base section, 34 . . . distal section, 35 . . . metacarpophalangeal joint, 40 . . . interphalangeal joint), 4 . . . index finger (11 . . . base portion, 12 . . . base section, 13 . . . middle section, 14 . . . distal section, 15 . . . metacarpophalangeal joint, 20 . . . proximal interphalangeal joint (interphalangeal joint), 22 . . . distal interphalangeal joint (interphalangeal joint)), 5 . . . middle finger, 6 . . . ring finger, 7 . . . little finger, 8 . . . wrist motor (one of two motors for performing pronation or supination operation and bending/extending operation of wrist portion), 9 . . . wrist motor (one of two motors for performing pronation or supination operation and bending or extending operation of wrist portion), 10 . . . thumb turning motor, 16 . . . finger motor, 17 . . . worm deceleration mechanism, 18 . . . worm, 19 . . . worm wheel (output gear), 21 . . . first driving link (link mechanism; driving link formed by two parts linked via elastic members), 23 . . . second driving link, 24 . . . first rod (one of two parts linked via elastic members), 25 . . . second rod (one of two parts linked via elastic members), 26 . . . coil spring (elastic member), 27 . . . coil spring (elastic member), 28 . . . first spur gear, 29 . . . second spur gear, 36 . . . thumb motor (finger motor), 37 . . . worm deceleration mechanism, 38 . . . worm, 39 . . . worm wheel (output gear), 41 . . . thumb driving link (link mechanism; driving link formed by two parts linked via elastic member), 42 . . . back portion, 43 . . . recessed portion, 44 . . . driver board (board for controlling), 45 . . . control board (board for controlling), 46 . . . hand cover, 47 . . . LAN terminal, 50 . . . first bevel gear (differential deceleration mechanism), 51 . . . second bevel gear (differential deceleration mechanism), 52 . . . third bevel gear (differential deceleration mechanism), 53 . . . fourth bevel gear (differential deceleration mechanism), 54 . . . first bevel gear (differential deceleration mechanism), 55 . . . second bevel gear (differential deceleration mechanism), 56 . . . third bevel gear (differential deceleration mechanism), 60 . . . first rod (one of two parts linked via elastic member), 61 . . . second rod (one of two parts linked via elastic member), 62 . . . coil spring (elastic member).

The invention claimed is:

1. A humanoid electric hand comprising:
a metacarpophalangeal joint configured to perform a bending or extending operation;
an interphalangeal joint of a finger configured to bend or extend in response to the bending or extending operation;
a link mechanism including a driving link formed by two parts, the link mechanism linking the interphalangeal joint with the metacarpophalangeal joint and configured to bend or extend the interphalangeal joint in response to a bending or extending operation of the metacarpophalangeal joint;
a finger motor linked to the metacarpophalangeal joint for performing a bending or extending operation and configured to drive a worm deceleration mechanism including an output gear configured to rotate and bend or extend the metacarpophalangeal joint; and
elastic members linking the two parts of the driving link and comprising a first elastic member and a second elastic member, the first elastic member having a first modulus of elasticity and configured to compress in response to a force acting on the driving link in a direction of bending a joint angle of the interphalangeal joint, the second elastic member having a second modulus of elasticity higher than the first modulus of elasticity and configured to compress in response to a force acting on the driving link in a direction of-extending the joint angle of the interphalangeal joint.

2. The humanoid electric hand according to claim 1, wherein
the second elastic member is configured to not extend when the first elastic member compresses.

3. The humanoid electric hand according to claim 1, further including a thumb having a mechanism with two degrees of freedom for performing a turning operation and a bending or extending operation.

4. The humanoid electric hand according to claim 3, wherein the mechanism of the thumb includes a thumb motor for performing the turning operation of the thumb, the thumb motor having a maximum output larger than that of the finger motor used for driving the bending or extending operation of each finger.

5. The humanoid electric hand according to claim 1, further including a wrist portion having a mechanism with two degrees of freedom for performing a pronation or supination operation and a bending or extending operation of the wrist portion.

6. The humanoid electric hand according to claim 5, wherein the mechanism of the wrist includes two motors and a differential deceleration mechanism for performing pronation or supination operation and the bending or extending operation of the wrist portion.

* * * * *